(12) United States Patent
Sampas

(10) Patent No.: US 8,478,537 B2
(45) Date of Patent: Jul. 2, 2013

(54) METHODS AND SYSTEMS FOR CLUSTERING BIOLOGICAL ASSAY DATA

(75) Inventor: Nicholas M. Sampas, San Jose, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 1111 days.

(21) Appl. No.: 12/208,130

(22) Filed: Sep. 10, 2008

(65) Prior Publication Data

US 2010/0076969 A1    Mar. 25, 2010

(51) Int. Cl.
*G06F 7/00*    (2006.01)

(52) U.S. Cl.
USPC ............................... 702/19; 703/11; 707/700

(58) Field of Classification Search
None
See application file for complete search history.

(56) References Cited

U.S. PATENT DOCUMENTS

| 6,421,668 B1 | 7/2002 | Yakhini et al. | |
|---|---|---|---|
| 2004/0053317 A1* | 3/2004 | Glinskii | 435/6 |
| 2005/0273269 A1 | 12/2005 | Yakhini et al. | |
| 2006/0190190 A1 | 8/2006 | Yakhini et al. | |

OTHER PUBLICATIONS

Leonowicz et al. (Leonowicz et al. J Neuroscience Methods 142 (2005) 17-26).*

* cited by examiner

*Primary Examiner* — Mary Zeman

(57) ABSTRACT

Methods for clustering a data set from a biological assay are provided. Aspects of the methods include applying statistical analyses to bisected subsets of the data at selected cut-of values to identify one or more break points in the data set. In certain aspects, the statistical analyses employed are based on determining the p-values of two-tailed t-tests calculated using the bisected data at each cut-off value. Aspects of the invention further include computer programming and systems which are configured to cluster data sets from biological assays according to the subject methods.

20 Claims, 5 Drawing Sheets

METHODS AND SYSTEMS FOR CLUSTERING BIOLOGICAL ASSAY DATA

INTRODUCTION

Traditional clustering methods generally require some preconceived knowledge of, or assumptions about, the data being analyzed. For example, in the case of k-means, that knowledge is the number of clusters expected, or in the case of other clustering methods, such as CAST (see U.S. Pat. No. 6,421,668), it is a minimal level of similarity or distance between the members of each cluster.

However, in the absence of such assumptions or preconceived knowledge, clustering data points in a data set containing two underlying distributions that are intermingled is difficult. This is especially the case when the underlying distributions in a single data set are close enough to each other such that the difference between the means of each distribution is small or comparable to the widths of the distributions themselves.

SUMMARY

Methods for clustering a data set from a biological assay are provided. Aspects of the methods include applying statistical analyses to bisected subsets of the data at selected cut-of values to identify one or more break points in the data set. In certain aspects, the statistical analyses employed are based on determining the p-values of two-tailed t-tests calculated using the bisected data at each cut-off value. Aspects of the invention further include computer programming and systems which are configured to cluster data sets from biological assays according to the subject methods.

Aspects of the subject invention include methods of clustering a data set from a biological assay including:
 a) obtaining a data set from a biological assay, wherein the data set comprises N measured values;
 b) sorting the data set from low (sample 1) to high (sample N) based on the measured values;
 c) selecting a set of cut-off points, wherein each of the cut-off points (k) is selected from sample 2 to sample N−2 of the data set;
 d) determining the best cut-off point from the set of cut-off points, comprising;
  i) for each cut-off point k, bisecting the data set into a first subset comprising samples 1 to k and a second subset comprising samples (k+1) to N; calculating the p-value of the measured values in the first and second subsets using a 2-tailed t-test; and calculating a modality score based on the p-value; and
  ii) determining the best cut-off point based on the modality score;
 e) clustering the samples into a first and second group at the best cut-off point if the modality score exceeds a threshold value; and
 f) providing the result of the clustering step (e) to a user in a user-readable format.

In certain embodiments, the two-tailed t-test is a Student's two-tailed t-test.

In certain embodiments, the modality score employs a correction coefficient.

In certain embodiments, the correction coefficient is a binomial correction coefficient B(N, k).

In certain embodiments, the binomial correction coefficient B(N, k) is:

$$N!/[k!(N-k)!].$$

In certain embodiments, the binomial correction coefficient B(N, k) is:

$$N!^{0.5}/[k!(N-k)!]^{0.5}.$$

In certain embodiments, the correction coefficient is based on an average p-value calculated using multiple random data sets, wherein each of the multiple random data sets has N values and wherein p-values for each of the multiple random data sets are calculated using the selected cut-off points for the data set.

In certain embodiments, the multiple random data sets are generated using one or more of: a random number generator and a random permutation of measured data.

In certain embodiments, the correction coefficient is based on a combination of the average p-value and an additional statistic.

In certain embodiments, the additional statistic is selected from: standard deviation of the average p-value and the intraquartile range (IQR) of the average p-value.

In certain embodiments, the method further comprises repeating the method iteratively or recursively on one or both of the first and second groups.

In certain embodiments, the biological assay is selected from the group consisting of: an array-based assay, an ELISA assay, a PCR assay, a RT-PCR assay, a quantitative RT-PCR assay, a flow cytometric assay, a reporter gene assay, and a high throughput screening assay.

Aspects of the present invention include systems for clustering a data set from a biological assay, the system including:
 (a) a communication module comprising an input manager for receiving input from a user and an output manager for communicating output to a user;
 (b) a processing module comprising a biological assay data clustering manager configured to:
  (i) receive a biological assay data set comprising N measured values from a user;
  (ii) sort the data set from low (sample 1) to high (sample N) based on the measured values;
  (iii) select a set of cut-off points, wherein each of the cut-off points (k) is selected from sample 2 to sample N−2 of the sorted data set;
  (iv) determine the best cut-off point from the set of cut-off points, comprising;
   1) for each cut-off point k, bisecting the data set into a first subset comprising samples 1 to k and a second subset comprising samples (k+1) to N; calculating the p-value of the measured values in the first and second subsets using a 2-tailed t-test; and calculating a modality score based on the p-value; and
   2) determining the best cut-off point based on the modality score;
  v) cluster the samples into a first and second group at the best cut-off point if the modality score exceeds a threshold value; and
  vi) provide the result of the clustering step (v) to the user in a user-readable format.

In certain embodiments, the two-tailed t-test is a Student's two-tailed t-test.

In certain embodiments, the modality score employs a binomial correction coefficient B(N, k).

In certain embodiments, the binomial correction coefficient B(N, k) is selected from: $N!/[k!(N-k)!]$ and $N!^{0.5}/[k!(N-k)!]^{0.5}$.

In certain embodiments, the modality score employs a correction coefficient based on an average p-value calculated using multiple random data sets, wherein each of the multiple random data sets has N values and wherein p-values for each of the multiple random data sets are calculated using the selected cut-off points for the data set.

In certain embodiments, the correction coefficient is based on a combination of the average p-value and an additional statistic selected from: standard deviation of the average p-value and the intra-quartile range (IQR) of the average p-value.

In certain embodiments, the biological assay data clustering manager is further configured to repeat steps (ii) to (v) iteratively or recursively on one or both of the first and second groups.

Aspects of the present invention include computer program products including a computer readable medium carrying one or more sequences of instructions for clustering a data set from a biological assay, wherein execution of one or more sequences of instructions by one or more processors causes the one or more processors to perform the steps of:
  a) receiving a data set from a biological assay from a user, wherein the data set comprises N measured values;
  b) sorting the data set from low (sample 1) to high (sample N) based on the measured values;
  c) selecting a set of cut-off points, wherein each of the cut-off points (k) is selected from sample 2 to sample N−2 of the data set;
  d) determining the best cut-off point from the set of cut-off points, comprising;
    i) for each cut-off point k, bisecting the data set into a first subset comprising samples 1 to k and a second subset comprising samples (k+1) to N; calculating the p-value of the measured values in the first and second subsets using a 2-tailed t-test; and calculating a modality score based on the p-value; and
    ii) determining the best cut-off point based on the modality score;
  e) clustering the samples into a first and second group at the best cut-off point if the modality score exceeds a threshold value; and
  f) providing the result of the clustering step (e) to the user in a user-readable format.

DEFINITIONS

Figure 1:
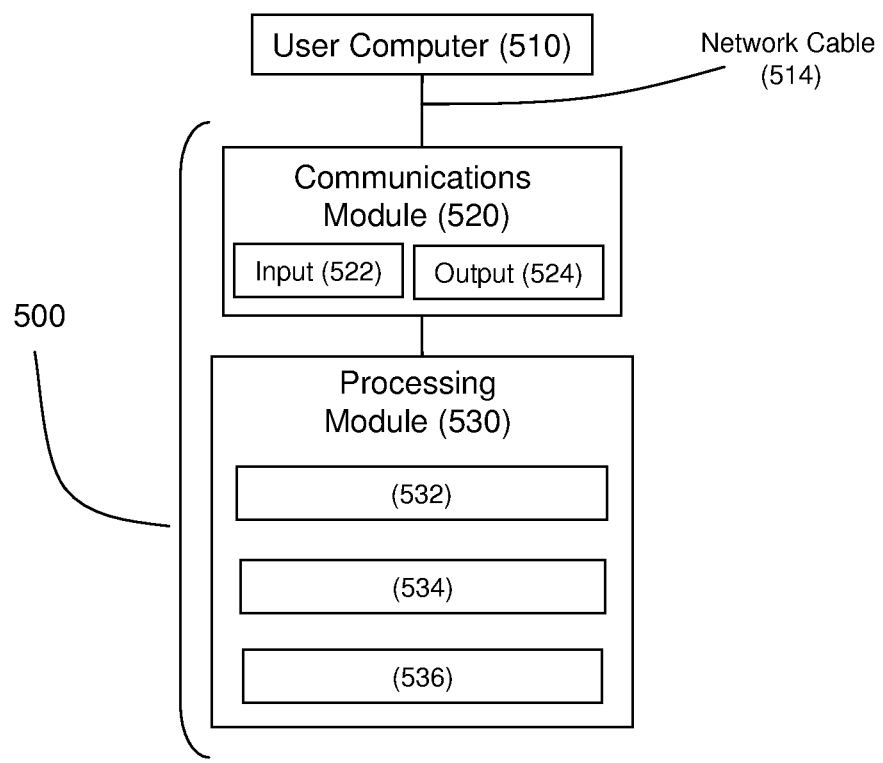
FIG. 1 schematically illustrates a system according to an embodiment of the invention.

The terms "biological assay data", "biological data", "biological data set", etc., as used herein refer to data derived from assays for detecting one or more target moieties in a biological sample (e.g., organism, cell, tissue, extract, secretion, etc.). The readout of such biological assays is a set of data point measurements (either direct or ratiometric measurements) that are reflective of the amount of the moiety or moieties of interest in the biological sample (or samples) being analyzed. Readouts of these biological assays can take a variety of forms, including fluorescent, calorimetric, radio-isotope, luminescent, enzymatic, etc. Exemplary biological assays that produce biological assay data include: array based assays (e.g., biopolymer arrays for comparative genome hybridization assays (CGH), nucleic acid hybridization assays, protein/ligand binding assays, etc.); ELISA assays; PCR assays (e.g., quantitative RT-PCR); flow cytometric analysis; reporter gene assays; high throughput screening assays; and the like.

The term "mixture", as used herein, refers to a combination of elements, that are interspersed and not in any particular order. A mixture is heterogeneous and not spatially separable into its different constituents. Examples of mixtures of elements include a number of different elements that are dissolved in the same aqueous solution, or a number of different elements attached to a solid support at random or in no particular order in which the different elements are not especially distinct. In other words, a mixture is not addressable. To be specific, an array of surface bound polynucleotides, as is commonly known in the art and described below, is not a mixture of capture agents because the species of surface bound polynucleotides are spatially distinct and the array is addressable.

"Isolated" or "purified" generally refers to isolation of a substance (compound, polynucleotide, protein, polypeptide, polypeptide, chromosome, etc.) such that the substance comprises the majority percent of the sample in which it resides. Typically in a sample a substantially purified component comprises 50%, preferably 80%-85%, more preferably 90-95% of the sample. Techniques for purifying polynucleotides and polypeptides of interest are well known in the art and include, for example, ion-exchange chromatography, affinity chromatography, flow sorting, and sedimentation according to density.

The term "assessing" and "evaluating" are used interchangeably to refer to any form of measurement, and includes determining if an element is present or not. The terms "determining," "measuring," and "assessing," and "assaying" are used interchangeably and include both quantitative and qualitative determinations. Assessing may be relative or absolute. "Assessing the presence of" includes determining the amount of something present, as well as determining whether it is present or absent.

The term "using" has its conventional application, and, as such, means employing, e.g. putting into service, a method or composition to attain an end. For example, if a program is used to create a file, a program is executed to make a file, the file usually being the output of the program. In another example, if a computer file is used, it is usually accessed, read, and the information stored in the file employed to attain an end. Similarly if a unique identifier, e.g., a barcode is used, the unique identifier is usually read to identify, for example, an object or file associated with the unique identifier.

The term "genome" refers to all nucleic acid sequences (coding and non-coding) and elements present in or originating from any virus, single cell (prokaryote and eukaryote) or each cell type and their organelles (e.g. mitochondria) in a metazoan organism. The term genome also applies to any naturally occurring or induced variation of these sequences that may be present in a mutant or disease variant of any virus or cell type. These sequences include, but are not limited to, those involved in the maintenance, replication, segregation, and higher order structures (e.g. folding and compaction of DNA in chromatin and chromosomes), or other functions, if any, of the nucleic acids as well as all the coding regions and their corresponding regulatory elements needed to produce and maintain each particle, cell or cell type in a given organism.

For example, the human genome consists of approximately $3 \times 10^9$ base pairs of DNA organized into distinct chromosomes. The genome of a normal diploid somatic human cell consists of 22 pairs of autosomes (chromosomes 1 to 22) and either chromosomes X and Y (males) or a pair of chromosome Xs (female) for a total of 46 chromosomes. A genome of a cancer cell may contain variable numbers of each chromosome in addition to deletions, rearrangements and amplification of any subchromosomal region or DNA sequence.

The terms "system" and "computer-based system" refer to the hardware means, software means, and data storage means used to analyze the information of the present invention. The minimum hardware of the computer-based systems of the present invention comprises a central processing unit (CPU), input means, output means, and data storage means. As such, any convenient computer-based system may be employed in the present invention. The data storage means may comprise any manufacture comprising a recording of the present information as described above, or a memory access means that can access such a manufacture.

A "processor" references any hardware and/or software combination which will perform the functions required of it. For example, any processor herein may be a programmable digital microprocessor such as available in the form of an electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

"Computer readable medium" as used herein refers to any storage or transmission medium that participates in providing instructions and/or data to a computer for execution and/or processing. Examples of storage media include floppy disks, magnetic tape, USB, CD-ROM, a hard disk drive, a ROM or integrated circuit, a magneto-optical disk, or a computer readable card such as a PCMCIA card and the like, whether or not such devices are internal or external to the computer. A file containing information may be "stored" on computer readable medium, where "storing" means recording information such that it is accessible and retrievable at a later date by a computer. A file may be stored in permanent memory.

With respect to computer readable media, "permanent memory" refers to memory that is permanently stored on a data storage medium. Permanent memory is not erased by termination of the electrical supply to a computer or processor. Computer hard-drive ROM (i.e. ROM not used as virtual memory), CD-ROM, floppy disk and DVD are all examples of permanent memory. Random Access Memory (RAM) is an example of non-permanent memory. A file in permanent memory may be editable and re-writable.

To "record" data, programming or other information on a computer readable medium refers to a process for storing information, using any convenient method. Any convenient data storage structure may be chosen, based on the means used to access the stored information. A variety of data processor programs and formats can be used for storage, e.g. word processing text file, database format, etc.

A "memory" or "memory unit" refers to any device which can store information for subsequent retrieval by a processor, and may include magnetic or optical devices (such as a hard disk, floppy disk, CD, or DVD), or solid state memory devices (such as volatile or non-volatile RAM). A memory or memory unit may have more than one physical memory device of the same or different types (for example, a memory may have multiple memory devices such as multiple hard drives or multiple solid state memory devices or some combination of hard drives and solid state memory devices).

In certain embodiments, a system includes hardware components which take the form of one or more platforms, e.g., in the form of servers, such that any functional elements of the system, i.e., those elements of the system that carry out specific tasks (such as managing input and output of information, processing information, etc.) of the system may be carried out by the execution of software applications on and across the one or more computer platforms represented of the system. The one or more platforms present in the subject systems may be any convenient type of computer platform, e.g., such as a server, main-frame computer, a work station, etc. Where more than one platform is present, the platforms may be connected via any convenient type of connection, e.g., cabling or other communication system including wireless systems, either networked or otherwise. Where more than one platform is present, the platforms may be co-located or they may be physically separated. Various operating systems may be employed on any of the computer platforms, where representative operating systems include Windows, MacOS, Sun Solaris, Linux, OS/400, Compaq Tru64 Unix, SGI IRIX, Siemens Reliant Unix, and others. The functional elements of system may also be implemented in accordance with a variety of software facilitators, platforms, or other convenient method.

Items of data are "linked" to one another in a memory when the same data input (for example, filename or directory name or search term) retrieves the linked items (in a same file or not) or an input of one or more of the linked items retrieves one or more of the others.

The term "monomer" as used herein refers to a chemical entity that can be covalently linked to one or more other such entities to form a polymer. Of particular interest to the present application are nucleotide "monomers" that have first and second sites (e.g., 5' and 3' sites) suitable for binding to other like monomers by means of standard chemical reactions (e.g., nucleophilic substitution), and a diverse element which distinguishes a particular monomer from a different monomer of the same type (e.g., a nucleotide base, etc.). In general, synthesis of nucleic acids of this type utilizes an initial substrate-bound monomer that is used as a building-block in a multi-step synthesis procedure to form a complete nucleic acid. A "biomonomer" references a single unit, which can be linked with the same or other biomonomers to form a biopolymer (e.g., a single amino acid or nucleotide with two linking groups, one or both of which may have removable protecting groups).

The terms "nucleoside" and "nucleotide" are intended to include those moieties which contain not only the known purine and pyrimidine bases, but also other heterocyclic bases that have been modified. Such modifications include methylated purines or pyrimidines, acylated purines or pyrimidines, alkylated riboses or other heterocycles. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like.

As used herein, the term "amino acid" is intended to include not only the L, D- and nonchiral forms of naturally occurring amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine), but also modified amino acids, amino acid analogs, and other chemical compounds which can be incorporated in conventional oligopeptide synthesis, e.g., 4-nitrophenylalanine, isoglutamic acid, isoglutamine, $\epsilon$-nicotinoyl-lysine, isonipecotic acid, tetrahydroisoquinoleic acid, $\alpha$-aminoisobutyric acid, sarcosine, citrulline, cysteic acid, t-butylglycine, t-butylalanine, phenylglycine, cyclohexylalanine, $\beta$-alanine, 4-aminobutyric acid, and the like.

The term "oligomer" is used herein to indicate a chemical entity that contains a plurality of monomers. As used herein, the terms "oligomer" and "polymer" are used interchangeably, as it is generally, although not necessarily, smaller "polymers" that are prepared using the functionalized substrates of the invention, particularly in conjunction with combinatorial chemistry techniques. Examples of oligomers and polymers include polydeoxyribonucleotides (DNA), polyribonucleotides (RNA), other polynucleotides which are C-glycosides of a purine or pyrimidine base, polypeptides (proteins), polysaccharides (starches, or polysugars), and other chemical entities that contain repeating units of like chemical structure. In the practice of the instant invention, oligomers will generally comprise about 2-50 monomers, preferably about 2-20, more preferably about 3-10 monomers.

The term "polymer" means any compound that is made up of two or more monomeric units covalently bonded to each other, where the monomeric units may be the same or different, such that the polymer may be a homopolymer or a heteropolymer. Representative polymers include peptides, polysaccharides, nucleic acids and the like, where the polymers may be naturally occurring or synthetic.

A "biopolymer" is a polymer of one or more types of repeating units. Biopolymers are typically found in biological systems (although they may be made synthetically) and may include peptides or polynucleotides, as well as such compounds composed of or containing amino acid analogs or non-amino acid groups, or nucleotide analogs or non-nucleotide groups. This includes polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in Watson-Crick type hydrogen bonding interactions. Polynucleotides include single or multiple stranded configurations, where one or more of the strands may or may not be completely aligned with another. For example, a "biopolymer" may include DNA (including cDNA), RNA, oligonucleotides, and PNA and other polynucleotides as described in U.S. Pat. No. 5,948,902 and references cited therein (all of which are incorporated herein by reference), regardless of the source.

The term "biomolecular probe" or "probe" means any organic or biochemical molecule, group or species of interest having a particular sequence or structure. In certain embodiments, a biomolecular probe may be formed in an array on a substrate surface. Exemplary biomolecular probes include polypeptides, proteins, oligonucleotide and polynucleotides. In certain embodiments, a probe is designed to bind specifically to a target under appropriate assay conditions (e.g., stringent hybridization conditions), where such a probe may be employed to detect the presence or absence of its corresponding target in a sample. In certain embodiments a probe is designed not to bind to any target present in a sample (e.g., a negative control probe).

The term "sample" as used herein relates to a material or mixture of materials, typically, although not necessarily, in fluid form, containing one or more components of interest.

A biomonomer fluid or biopolymer fluid refers to a liquid containing either a biomonomer or biopolymer, respectively (typically in solution).

The term "peptide" as used herein refers to any polymer compound produced by amide formation between an $\alpha$-carboxyl group of one amino acid and an $\alpha$-amino group of another group.

The term "oligopeptide" as used herein refers to peptides with fewer than about 10 to 20 residues, i.e., amino acid monomeric units.

The term "polypeptide" as used herein refers to peptides with more than 10 to 20 residues.

The term "protein" as used herein refers to polypeptides of specific sequence of more than about 50 residues.

The term "nucleic acid" as used herein means a polymer composed of nucleotides, e.g., deoxyribonucleotides or ribonucleotides, or compounds produced synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "oligonucleotide" as used herein denotes single-stranded nucleotide multimers of from about 10 up to about 200 nucleotides in length, e.g., from about 25 to about 200 nt, including from about 50 to about 175 nt, e.g. 150 nt in length The term "polynucleotide" as used herein refers to single- or double-stranded polymers composed of nucleotide monomers of generally greater than about 100 nucleotides in length.

An "array," or "chemical array" used interchangeably includes any one-dimensional, two-dimensional or substantially two-dimensional (as well as a three-dimensional) arrangement of addressable regions bearing a particular chemical moiety or moieties (such as ligands, e.g., biopolymers such as polynucleotide or oligonucleotide sequences (nucleic acids), polypeptides (e.g., proteins), carbohydrates, lipids, etc.) associated with that region. As such, an addressable array includes any one or two or even three-dimensional arrangement of discrete regions (or "features") bearing particular biopolymer moieties (for example, different polynucleotide sequences) associated with that region and positioned at particular predetermined locations on the substrate (each such location being an "address"). These regions may or may not be separated by intervening spaces. In the broadest sense, the arrays of many embodiments are arrays of polymeric binding agents, where the polymeric binding agents may be any of: polypeptides, proteins, nucleic acids, polysaccharides, synthetic mimetics of such biopolymeric binding agents, etc. In many embodiments of interest, the arrays are arrays of nucleic acids, including oligonucleotides, polynucleotides, cDNAs, mRNAs, synthetic mimetics thereof, and the like. Where the arrays are arrays of nucleic acids, the nucleic acids may be covalently attached to the arrays at any point along the nucleic acid chain, but are generally attached at one of their termini (e.g. the 3' or 5' terminus). Sometimes, the arrays are arrays of polypeptides, e.g., proteins or fragments thereof.

In those embodiments where an array includes two more features immobilized on the same surface of a solid support, the array may be referred to as addressable. An array is "addressable" when it has multiple regions of different moieties (e.g., different polynucleotide sequences) such that a region (i.e., a "feature" or "spot" of the array) at a particular predetermined location (i.e., an "address") on the array will detect a particular target or class of targets (although a feature may incidentally detect non-targets of that feature). Array features are typically, but need not be, separated by intervening spaces. In the case of an array, the "target" will be referenced as a moiety in a mobile phase (typically fluid), to be detected by probes ("target probes") which are bound to the substrate at the various regions. However, either of the "target" or "probe" may be the one which is to be evaluated by the other (thus, either one could be an unknown mixture of analytes, e.g., polynucleotides, to be evaluated by binding with the other).

When two items are "associated" with one another they are provided in such a way that it is apparent one is related to the other such as where one references the other. For example, an array identifier can be associated with an array by being on the array assembly (such as on the substrate or a housing) that carries the array or on or in a package or kit carrying the array assembly. "Stably attached" or "stably associated with" means an item's position remains substantially constant where in certain embodiments it may mean that an item's position remains substantially constant and known.

The terms "hybridizing specifically to" and "specific hybridization" and "selectively hybridize to," as used herein refer to the binding, duplexing, or hybridizing of a nucleic acid molecule preferentially to a particular nucleotide sequence under stringent conditions.

"Hybridizing" and "binding", with respect to polynucleotides, are used interchangeably.

The term "stringent assay conditions" as used herein refers to conditions that are compatible to produce binding pairs of nucleic acids, e.g., surface bound and solution phase nucleic acids, of sufficient complementarity to provide for the desired level of specificity in the assay while being less compatible to the formation of binding pairs between binding members of insufficient complementarity to provide for the desired specificity. Stringent assay conditions are the summation or combination (totality) of both hybridization and wash conditions.

"Stringent hybridization conditions" and "stringent hybridization wash conditions" in the context of nucleic acid hybridization (e.g., as in array, Southern or Northern hybridizations) are sequence dependent, and are different under different experimental parameters. Stringent hybridization conditions that can be used to identify nucleic acids within the scope of the invention can include, e.g., hybridization in a buffer comprising 50% formamide, 5×SSC, and 1% SDS at 42° C., or hybridization in a buffer comprising 5×SSC and 1% SDS at 65° C., both with a wash of 0.2×SSC and 0.1% SDS at 65° C. Exemplary stringent hybridization conditions can also include hybridization in a buffer of 40% formamide, 1 M NaCl, and 1% SDS at 37° C., and a wash in 1×SSC at 45° C. Alternatively, hybridization to filter-bound DNA in 0.5 M NaHPO$_4$, 7% sodium dodecyl sulfate (SDS), 1 mM EDTA at 65° C., and washing in 0.1×SSC/0.1% SDS at 68° C. can be employed. Yet additional stringent hybridization conditions include hybridization at 60° C. or higher and 3×SSC (450 mM sodium chloride/45 mM sodium citrate) or incubation at 42° C. in a solution containing 30% formamide, 1M NaCl, 0.5% sodium sarcosine, 50 mM MES, pH 6.5. Those of ordinary skill will readily recognize that alternative but comparable hybridization and wash conditions can be utilized to provide conditions of similar stringency.

In certain embodiments, the stringency of the wash conditions sets forth the conditions which determine whether a nucleic acid is specifically hybridized to a surface bound nucleic acid. Wash conditions used to identify nucleic acids may include, e.g.: a salt concentration of about 0.02 molar at pH 7 and a temperature of at least about 50° C. or about 55° C. to about 60° C.; or, a salt concentration of about 0.15 M NaCl at 72° C. for about 15 minutes; or, a salt concentration of about 0.2×SSC at a temperature of at least about 50° C. or about 55° C. to about 60° C. for about 15 to about 20 minutes; or, the hybridization complex is washed twice with a solution with a salt concentration of about 2×SSC containing 0.1% SDS at room temperature for 15 minutes and then washed twice by 0.1×SSC containing 0.1% SDS at 68° C. for 15 minutes; or, equivalent conditions. Stringent conditions for washing can also be, e.g., 0.2×SSC/0.1% SDS at 42° C.

A specific example of stringent assay conditions is rotating hybridization at 65° C. in a salt based hybridization buffer with a total monovalent cation concentration of 1.5 M (e.g., as described in U.S. patent application Ser. No. 09/655,482 filed on Sep. 5, 2000, the disclosure of which is herein incorporated by reference) followed by washes of 0.5×SSC and 0.1× SSC at room temperature.

Stringent assay conditions are hybridization conditions that are at least as stringent as the above representative conditions, where a given set of conditions are considered to be at least as stringent if substantially no additional binding complexes that lack sufficient complementarity to provide for the desired specificity are produced in the given set of conditions as compared to the above specific conditions, where by "substantially no more" is meant less than about 5-fold more, typically less than about 3-fold more. Other stringent hybridization conditions may also be employed, as appropriate.

"Contacting" means to bring or put together. As such, a first item is contacted with a second item when the two items are brought or put together, e.g., by touching them to each other.

"Depositing" means to position or place an item at a location, or otherwise cause an item to be so positioned or placed at a location. Depositing includes contacting one item with another. Depositing may be manual or automatic, e.g., "depositing" an item at a location may be accomplished by automated robotic devices.

By "remote location," it is meant a location other than the location at which the array (or referenced item) is present and hybridization occurs (in the case of hybridization reactions). For example, a remote location could be another location (e.g., office, lab, etc.) in the same city, another location in a different city, another location in a different state, another location in a different country, etc. As such, when one item is indicated as being "remote" from another, what is meant is that the two items are at least in different rooms or different buildings, and may be at least one mile, ten miles, or at least one hundred miles apart. "Communicating" information means transmitting the data representing that information as signals (e.g., electrical, optical, radio signals, and the like) over a suitable communication channel (for example, a private or public network). "Forwarding" an item refers to any means of getting that item from one location to the next, whether by physically transporting that item or otherwise (where that is possible) and includes, at least in the case of data, physically transporting a medium carrying the data or communicating the data.

It will also be appreciated that throughout the present application, that words such as "cover", "base" "front", "back", "top", are used in a relative sense only. The word "above" used to describe the substrate and/or flow cell is meant with respect to the horizontal plane of the environment, e.g., the room, in which the substrate and/or flow cell is present, e.g., the ground or floor of such a room.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present, and, thus, the description includes structures wherein a non-hydrogen substituent is present and structures wherein a non-hydrogen substituent is not present.

DETAILED DESCRIPTION

Methods of clustering data sets from a biological assay based on the values of the data set itself are provided. Aspects of the methods include applying statistical analyses to bisected subsets of the data at selected cut-of values to identify one or more break points in the data set. As described in detail below, the statistical analyses employed are based on determining the p-values of two-tailed t-tests calculated using the bisected data at each cut-off value. Using this method iteratively or recursively can segregate the data into two or more clusters. Aspects of the invention further include computer programming and systems that include the same which are configured to cluster data sets from biological assays.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Methods and Systems

As generally employed in data analysis, two-tailed t-tests are employed to determine whether two different sets of data points (or measurements) from different data sets are randomly drawn to two distinct distributions or from a single distribution. In most applications, two-tailed t-tests are applied to cases where there are two independent sets of data points that are already partitioned.

In contrast to this application of two-tailed t-tests, we describe herein methods and systems in which two-tailed t-tests are employed to cluster a single, un-clustered (or un-segregated) data set. As will be described in detail below, such clustering finds use in the analysis of a variety of types of experimental data, including data sets comprised of ratiometric values (e.g., CGH data, microarray data) or non-ratiometric values (e.g., quantitative PCR assays, ELISAs assays, etc.). As such, certain aspects of the present invention are drawn to the clustering of discreet data points in a single, un-clustered data set from an experimental biological assay. The results of such clustering can be provided to a user in a user readable format (e.g., associated with a physical memory element that can be accessed by a user) with the cluster to which each member of the data set has been assigned indicated. Therefore, in certain embodiments, the subject systems and methods provide a means of distinguishing the members of a lower state distribution(s) and those of an upper state distribution(s) in a single un-clustered (or un-partitioned) data set.

As indicated above, the difficulty in clustering the data points in a single data set arises when the two underlying distributions are close enough to each other that the difference between the means is small by comparison to the widths of the distributions. Because of this, the underlying distributions have intermingled measurements, making them difficult to distinguish in the absence of further information. Moreover, the partitioning of measurements from two overlapping distributions at a sharply defined breakpoint alters the shape of each of the underlying distributions.

Below is described a general method according to aspects of the present invention for clustering a set of CGH data, where the clustering can be employed for data evaluation (e.g., for copy number variation (CNV) analysis). While the description below described clustering CGH data, other types of experimental data can be analyzed using the subject systems and methods, including but not limited to: microarray data (e.g., for RNA transcript expression), PCR data (e.g., quantitative PCR or RT-PCR), ELISA assay data, protein microarray data, flow cytometric data, high throughput assay data, and the like. As such, the systems and methods described herein can be applied to either direct measurements of discrete values (both linear & nonlinear) as well as ratiometric measurements comprised of ratios of discrete values (e.g., as obtained from standard CGH assays).

In this exemplary description, a CGH data set is obtained containing measurements for N data points (e.g., data points for N genomic probes employed in a CGH assay). The measurements may take a variety of forms, for example as a set of measurements of direct signals or as a set of ratios of measurements (e.g., log ratios of measurements of a control sample signal to a to a test sample signal for each data point). In this example, the data points of undetermined copy number status; in other words, the data points are not segregated or identified in ay other fashion according to a copy number.

Once obtained, the data set, which contains measurements for N distinct data points (e.g., one for each of N probes employed in the assay), is sorted from low to high based on the value of each the measured values, with the first sample having the lowest measurement and the Nth sample having the highest measurement (i.e., from 1 to N). A range of cut-off points is then determined for the sorted data set measurements, where each cut-off point (denoted as k, where k is the data point number having measured value $k_{val}$) in the range of cut-off points is selected from among the sorted data points. In certain embodiments, cut-off points are selected from the range of data points between data point 2 to data point N−2, inclusive. The number of cut-off points can vary, where in certain embodiments, every data point between data point 2 and N−2, inclusive, is selected, whereas in certain other embodiments, only a subset of the data points between 2 and N−2 are used. As such, the number of cut-off points employed can range from 1 to N−3.

For each cut-off point k in the range of cut-off points, the complete set of data point measurements (i.e., from data points 1 to N) is bisected to form two sets of data point measurements: the first set including data points below and including the specific cut-off point for data point k (i.e., all data points≦k), and all data points above the specific cut-off point (i.e., data points>k). For each cut off point k, the p-value of a two-tailed t-test is calculated for the data point measurements in the two sets of data point measurements produced at that cut-off point k. The one that we have based these calculations on is Student's two-tailed t-test. In certain embodiments, a Student's two-tailed t-test is employed. The functional form of Student's two-tailed t-test takes as arguments: the mean values, variances of two sets of measurements, and the numbers of distinct measurements that were averaged to generate each mean value. As applied here, the mean value is the mean across each subset of measurements above and below the cut-off point k, standard deviation σ (or the variance $\sigma^2$) for the set, and the number of measurements in the set (i.e., k and N−k). In certain embodiments, the variance may include components due to noise values associated with each measurement.

Once the p-value for the measurements at a selected cut-off point is calculated, a modality score based on the calculated p-value is determined. The modality score can be calculated after each p-value for a cut-off point is calculated or may be calculated after all p-values for all cut-off points have been calculated. In general, any modality score that uses a p-value calculated at a cut-off point can be employed. The modality score may be applied to a sorted set of data point measurements either at each cut-off point, a subset of sampled cut-off points, or iteratively determined cut-off points.

In one embodiment, the following modality score is used:

$$\text{Modality Score} = -\log(p(N,k)*C)$$

where p(N,k) is the p-value calculated for the data measurements at cut-off point k for a data set having N data points and C is a correction coefficient. In certain embodiments, C is a binomial coefficient [B(N,k)]. In certain embodiments, the binomial coefficient is:

$$B(N,k) = N!/[k!(N-k)!].$$

In certain other embodiments, the square root of the binomial coefficient is employed as C:

$$B(N,k) = N!^{0.5}/[k!(N-k)!]^{0.5}.$$

In another embodiment, C is calculated from a numerical simulation of the data using a random noise generator, and using the averaged p-value of random data to correct the p-value of the real data for the same values of N and k. In certain embodiments, a random permutation of measured data is used instead of a random number generator. For example, a score which is a functional combination of the averaged p-value (e.g., average log(p-value)) of the random data (or random permutation of measured data) and another statistic is used. For example, C can be calculated as:

$$\langle\text{p-value}\rangle + q*\sigma(\text{p-value}),$$

or $$\langle\text{p-value}\rangle + q*\text{IQR}(\text{p-value}),$$

where <p-value> is the calculated p-value of the data set being analyzed, (p-value) is the average p-value of the random data (or random permutation of measured data), σ is the standard deviation of (p-value), IQR is the IntraQuartile-Range, and q is simply a multiplication factor, where in certain embodiments q corresponds to a significance level of interest.

In yet another embodiment, C is calculated in the functional form of a hyperbola, centered at k=N/2 and adjusted to match the log(p-value) curve.

Once the modality score and C are defined, the best cut-off point is identified from the selected set of cut-off points. In certain embodiments, the best cut-off point is identified as the cut-off point with the maximal normalized p-value. If the maximal normalized p-value of the best cut-off point exceeds a minimal value (a threshold value), then the data point measurements are segregated into two clusters at that cut-off point (which is also referred to as a break point).

In certain embodiments, the data set will be divided into two clusters if: 1) the modality score exceeds a threshold; and 2) the difference between the two average values for the two potential clusters exceeds a threshold value. The threshold may itself depend on the mean values of the two potential clusters. For example if either one of the potential clusters has a mean value that is below zero, then the set will only be broken into clusters at that point if the difference between the two average values is greater than 0.2.

In certain embodiments, the data set will be divided into two clusters if: 1) the modality score exceeds a threshold; and 2) the minimal difference between elements of two adjacent potential clusters is greater than some threshold value.

In many cases the data may not represent only two discrete states, but rather several or even many discrete states (i.e. for a data set that is to be segregated into 3 or more clusters). In cases where the number of distinct states is relatively small, one effective method for determining all the best break points between them is to apply the clustering method iteratively (or even recursively). The iterative process can be done to a maximal depth (e.g., a cluster analysis may be set up for segregating a data set into 4 separate clusters) or until the minimal number samples is encountered in a data cluster (i.e., a data cluster having 4 data points or fewer). This is done by first applying a binary modal analysis on the whole set of numbers or measurements, then, once a first break point is established, applying it to each cluster independently. This approach can then be applied iteratively on each cluster, where any "best" cut-off value for the data points in a cluster is identified as a break point if it meets a minimal threshold criterion.

In certain embodiments, the total scores for each significant cluster can be summed along with the scores of their parent clusters. For example, a list of total scores can be maintained in which each subset of scores for each iterative cutoff is added to this superset of scores in cases for which nested subsets of elements form significant clusters. In this way, a hierarchical tree can be generated for one-dimensional clustering. In certain other embodiments, the modality score for every segregation can be kept track of independently and reported for subsequent filtering.

If there are a large number of distinct states within a data set, it may be useful to draw artificial boundaries at a spacing that is somewhat larger than the anticipated spacing of the discrete underlying quanta. Once the existing boundaries within the data itself have been established (e.g., after application of the clustering methods described herein), the artificial boundaries can be removed and the scores recalculated.

As indicated above, ratiometric CGH measurements are comprised of measurements for an unknown sample compared to corresponding measurements for a reference sample, the corresponding measurements being derived from a specific CGH probe. In certain embodiments, the discrete state (e.g., copy number) of the reference sample is known, making calling the copy number for any identified cluster (as detailed above) rather straightforward.

However, in certain embodiments, the discrete state of the reference sample is unknown. In such cases, a data set having a sufficient number of data points and in which multiple copy number states are represented in the reference sample, it is possible to deduce the reference sample copy number states. The distributions of the clusters determined as detailed above (also called modes) can be fitted to any of several distinct sets of values. For example, if the copy number state of the reference is 2, then the anticipated ratio values for different modes of the data set are 0, 0.5, 1.0, 1.5, 2.0, 2.5, 3.0 (etc.) with their corresponding $\log_2$ ratio values being −Inf, −1.0, 0.585, 1, 1.322 (etc.). Using similar analysis, if the reference state is 1 copy, the $\log_2$ ratio values would be −Inf, 0, 1.0, 1.585, 2.0, 2.322, 2.585 (etc.).

In practice these fold change values are typically somewhat reduced for a number of reasons, including non-specific binding of labeled targets to the CGH probes, finite dynamic range, and noise in the measurements of the signals themselves. Therefore, by measuring the average signals or log ratios for each cluster (or mode), and by fitting with a simple ratiometric model that estimates these additive signal components, the absolute copy number states of both the reference and unknown sample can be deduced.

The result of the subject clustering method is then output to one or more users in some manner, where the outputting results in a physical transformation of to a useful, concrete and tangible result. For example, the result may be made accessible to a user in some manner so as to make it a tangible result. The result may be made accessible in a number of different manners, such as by displaying it to a user, e.g., via a graphical user interface (GUI), by recording it onto a physical medium, e.g., a computer readable medium, and human readable medium, e.g., paper, spreadsheets, databases, etc. The above embodiments are merely exemplary.

In certain embodiments, the subject methods include a step of transmitting data or results to a remote location (e.g., by communicating, forwarding, etc.). The data may be transmitted to the remote location for further evaluation and/or use. Any convenient telecommunications means may be employed for transmitting the data, e.g., facsimile, modem, internet, etc.

The invention also provides a variety of computer-related embodiments. Specifically, the biological assay data analysis methods described herein may be performed using a computer. Accordingly, the invention provides a computer-based system for clustering biological assay data employing the methods described herein and providing the results in a tangible form to a user.

In certain embodiments, the methods are coded onto a computer-readable medium in the form of "programming", where the term "computer readable medium" as used herein refers to any storage or transmission medium that participates in providing instructions and/or data to a computer for execution and/or processing. Examples of storage media include floppy disks, magnetic tape, CD-ROM, a hard disk drive, a ROM or integrated circuit, a magneto-optical disk, or a computer readable card such as a PCMCIA card and the like, whether or not such devices are internal or external to the computer. A file containing information may be "stored" on computer readable medium, where "storing" means recording information such that it is accessible and retrievable at a later date by a computer.

In certain embodiments, the computer readable medium is a medium carrying one or more sequences of instructions for clustering biological assay data, wherein execution of one or more sequences of instructions by one or more processors causes the one or more processors to perform the steps of:

a) sorting a biological data set from low (sample 1) to high (sample N) based on the measured values of the data points in the set;

b) selecting a set of cut-off points k from sample 2 to sample N−2 of the data set;

c) determining the best cut-off point from the set of cut-off points using the following steps: 1) for each cut-off point k, bisecting the data set into a first subset having samples 1 to k and a second subset having samples (k+1) to N; calculating the p-value of the measured values in the first and second subsets using a 2-tailed t-test; and calculating a modality score based on the p-value; and 2) determining the best cut-off sample based on the modality score;

d) clustering the samples into a first and second group at the best cut-off point if the modality score exceeds a threshold value; and e) providing the result of the clustering step (d) to a user in a user-readable format.

Aspects of the invention further include systems, e.g., computer based systems, which are configured to cluster biological assay data sets.

Embodiments of the subject systems include the following components: (a) a communications module for facilitating information transfer between the system and one or more users, e.g., via a user computer, as described below; and (b) a processing module for performing one or more tasks involved in the clustering methods of the present invention. In certain embodiments, the subject systems may be viewed as being the physical embodiment of a web portal, where the term "web portal" refers to a web site or service, e.g., as may be viewed in the form of a web page, that offers a broad array of resources and services to users via an electronic communication element, e.g., via the Internet.

FIG. 1 provides a view of a representative biological assay data clustering system according to an embodiment of the subject invention. In FIG. 1, system 500 includes communications module 520 and processing module 530, where each module may be present on the same or different platforms, e.g., servers, as described above.

The communications module includes the input manager 522 and output manager 524 functional elements. Input manager 522 receives information from a user, e.g., over the Internet. Input manager 522 processes and forwards this information to the processing module 530. These functions are implemented using any convenient method or technique. Another of the functional elements of communications module 520 is output manager 524. Output manager 524 provides information assembled by processing module 530 to a user, e.g., over the Internet. The presentation of data by the output manager may be implemented in accordance with any convenient methods or techniques. As some examples, data may include SQL, HTML or XML documents, plain text, email or other files, or data in other forms. The data may include Internet URL addresses so that a user may retrieve additional SQL, HTML, XML, or other documents or data from remote sources.

The communications module 520 may be operatively connected to a user computer 510, which provides a vehicle for a user to interact with the system 500. User computer 510, shown in FIG. 1, may be a computing device specially designed and configured to support and execute any of a multitude of different applications. Computer 510 also may be any of a variety of types of general-purpose computers such as a personal computer, network server, workstation, or other computer platform now or later developed. Computer 510 may include components such as a processor, an operating system, a graphical user interface (GUI) controller, a system memory, memory storage devices, and input-output controllers. There are many possible configurations of the components of computer 510 and some components are not listed above, such as cache memory, a data backup unit, and many other devices.

In certain embodiments, a computer program product is described comprising a computer usable medium having control logic (computer software program, including program code) stored therein. The control logic, when executed by the processor the computer, causes the processor to perform functions described herein. In other embodiments, some functions are implemented primarily in hardware using, for example, a hardware state machine. Implementation of the hardware state machine so as to perform the functions described herein may be accomplished using any convenient method and techniques.

In certain embodiments, a user employs the user computer to enter information into and retrieve information from the system. As shown in FIG. 1, computer 510 is coupled via network cable 514 to the system 500. Additional computers of other users and/or administrators of the system in a local or wide-area network including an Intranet, the Internet, or any other network may also be coupled to system 500 via cable 514. It will be understood that cable 514 is merely representative of any type of network connectivity, which may involve cables, transmitters, relay stations, network servers, wireless communication devices, and many other components not shown suitable for the purpose. Via user computer 510, a user may operate a web browser served by a user-side Internet client to communicate via Internet with system 500. System 500 may similarly be in communication over Internet with other users, networks of users, and/or system administrators, as desired.

As reviewed above, the systems include various functional elements that carry out specific tasks on the platforms in response to information introduced into the system by one or more users. In FIG. 1, elements 532, 534 and 536 represent three different functional elements of processing module 530. While three different functional elements are shown, it is noted that the number of functional elements may be more or less, depending on the particular embodiment of the invention. Functional elements that may be carried out by the processing module including a functional element configured to cluster a data set from a biological assay according to an embodiment of the invention, e.g., as described above.

Utility

As indicated above, the systems, methods and computer program products of the subject invention find use in analyzing a variety of types of biological assay data. For example, aspects of the subject invention have applications to clustering, classification and class discovery, for biological assays that employ array technology. These include, without limitation, such assays as comparative genome hybridization analyses (CGH), copy number variation analyses (CNV), gene expression analyses (e.g., both protein or nucleic acid-based), and other array-based assays for detecting the presence of other biomolecules (e.g., carbohydrates). In addition, aspects of the subject invention find use in analyzing data from other types of biological assays, including ELISA assays, PCR assays (e.g., RT-PCR, quantitative RT-PCR, etc.), flow cytometric data, reporter gene assays, high throughput screening (HTS) assay data (e.g., HTS assays having a readily detectable readout, e.g., fluorescent or calorimetric), etc. As such, aspects of the subject invention find use in analyzing virtually any data set of measurements from a biological assay that produces measurements of small integral values or ratios of small integers for which underlying distributions of the data points are desired. Furthermore, the measurements analyzed raw results (such as fluorescence intensity readings for each feature in one or more color channels) or may be processed results. Processed results include, but are not limited to, those obtained by subtracting a background measurement, by rejecting a reading that is above/below a predetermined threshold, normalized results, etc.

As noted above, one important area of CGH analysis is in the genotyping of copy-number variations (CNVs). One example of a common variant is the simple deletion variant. For example, consider a variant for which an allele is either present or not present on a given chromosome. If the chromosome is autosomal, then either chromosome can have an allele that is present or null for a sequence of DNA that hybridizes to one or more probes. In this case, the possible copy number states are zero, one or two copies per cell. As such, a data set from such a CNV assay can be analyzed according to aspects of the present invention to determine the best break point for segregating the data values into each of these copy number categories.

As another example, a data set from a gene expression assay can be analyzed according to aspects of the present invention to determine the best break point for segregating the data values into expression-level categories (e.g., no expression, low expression, moderate expression, etc.), where the categories can be relative (e.g., compared to a reference value) or absolute (e.g., for quantitative analysis).

As yet another example, a data set from a flow cytometric assay can be analyzed according to aspects of the present invention to computationally identifying gate settings to apply to the analyzed population. In such embodiments, populations having negative, low, moderate and/or high levels of expression can be identified (e.g., gated). In multi-parameter flow cytometry, the dataset can be gated (or segregate) based on the level of each (or a subset) of detection channels (e.g., FITC, PE, Cy5PE, forward scatter and/or side-scatter).

EXAMPLES

Consider a set of values $x_i$ from distribution $D_1$, and set of values $y_i$ from distribution $D_2$, but which are randomly intermingled and for which the mean $<y_i>$ is greater than the mean $<x_i>$. What we would like to do is to separate the set of values $x_i$ from $y_i$. If we choose values randomly, the probability of selecting the correct set is exceedingly small, but if we sort the values from low to high and then partition at some appropriate place (e.g., towards the middle of the set), we can enrich the higher set for $y_i$ values and the lower set for $x_i$ values. If the distributions are sufficiently separated, then the best place to set such a breakpoint may very well be at the largest gap between adjacent points.

However, if the two distributions are close together and overlap, then we are not likely to get a perfect separation of distributions by any sort-based cut-off point. Therefore, our approach is to apply a correction to the two-tailed t-test with which we can identify the best cut-off point and partition the two combined distributions. As described in general above, we first sort the data points based on their measurement values from low to high, with the lowest value data point being data point 1 and the highest value data point being data point N (where n is the number of data points). We then partition the data at all possible cut-off points while maintaining a minimal number of data points in each partitioned set. For example, the lowest cut-off point ($k_{min}$) would be data point 2 and the highest cut-off point ($k_{max}$) would be data point N-$k_{min}$ (or N-2, in this case). At each partitioning, we apply the two-tailed t-test with an appropriate normalization Coefficient (e.g., as described above). If properly normalized, the result will be homogeneous for all possible cutoffs for a random sampling of data that is derived from the same data distribution when averaged across a sufficient number of samplings.

Figure 2:
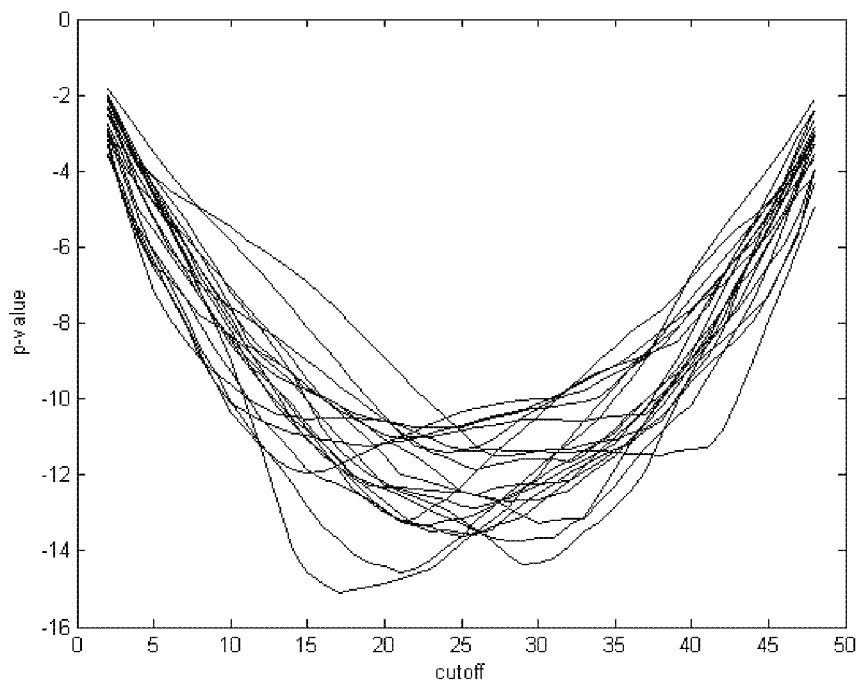
FIG. 2 shows a graph of p-values from two-tailed t-tests for multiple sets of random numbers (each set represented by a single line in the graph, where N=50) drawn from a normal distribution and partitioned by analyzing at 47 different cut-offs, each between the $2^{nd}$ and $48^{th}$ values, inclusive.

To determine what such a correction curve should look like, we can generate random data point values drawn from a normal distribution and calculate the p-values for all cut-off values along the sorted list of data points (i.e., sorted from low to high data value). An example of such a correction curve for multiple different data sets having 50 data points (i.e., N=50) is show in FIG. 2. By repeating this analysis for a large enough set of random numbers, we can estimate the ideal shape of a correction curve for a given distribution.

Figure 3:
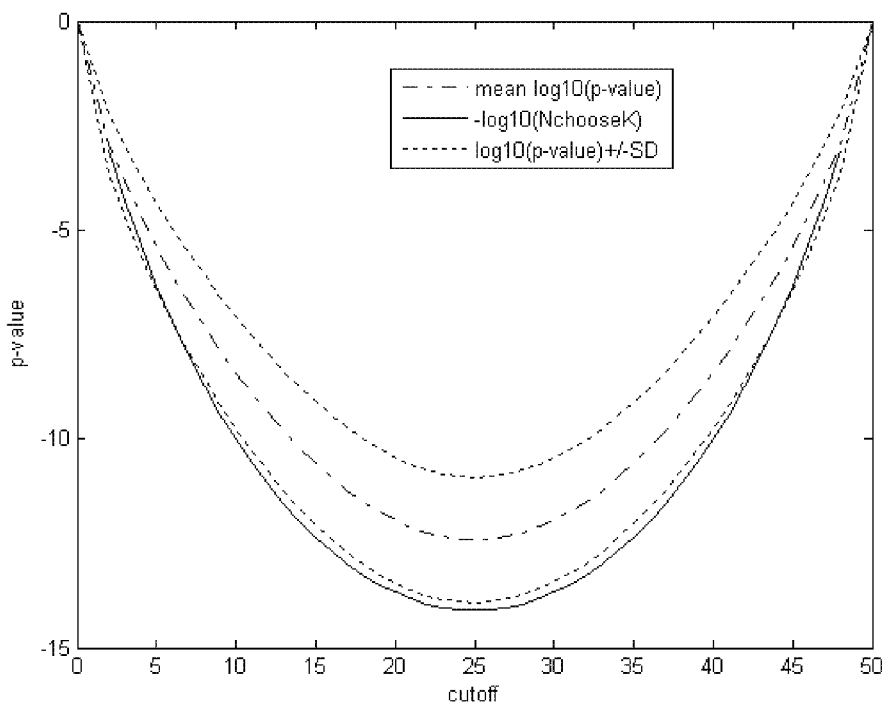
FIG. 3 shows average p-values for a sorted partitioning of N=50, k=from 2 to 48. Standard deviations of the average values are shown as error limits in dotted lines [labeled: log 10(p-value)+/−SD]. The binomial coefficient (N-chose-k) is displayed as solid line [labeled: −log 10(NchooseK)], and the dashed line is the mean p-value [labeled: mean log 10(p-value)]. All these are all plotted on a $\log_{10}$ scale.
Figure 4:
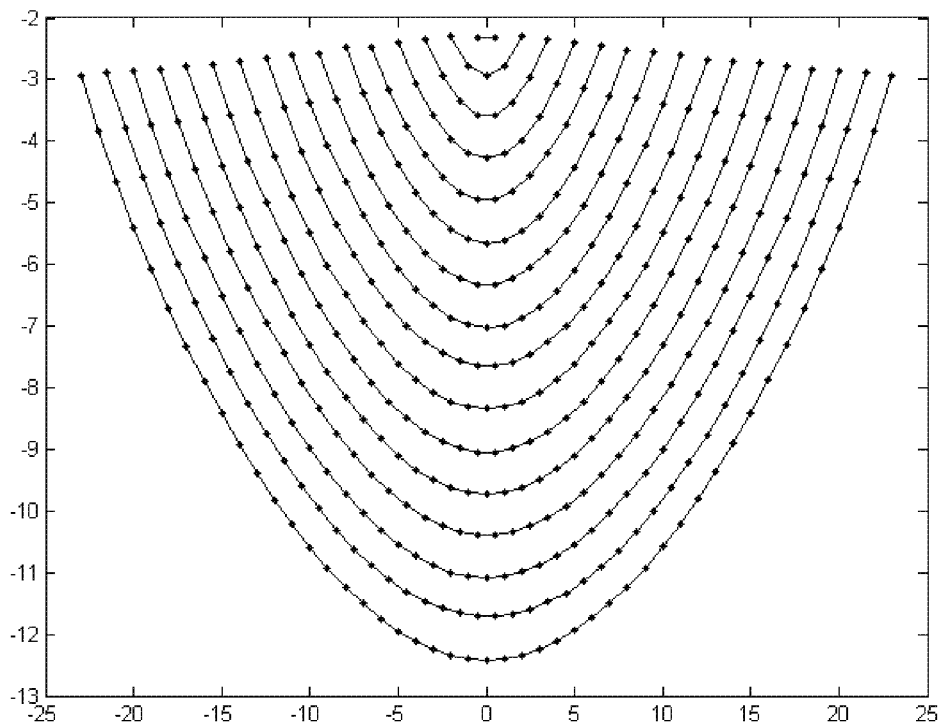
FIG. 4 shows $\log_{10}$ of the average p-values for a sorted partitioning of data sets having different numbers of values (N). In this figure, the average p-values for all possible sorted partitions (with a minimum partition size of 2) are shown for every third N value from N=2 to N=47.

An example of such an average of log(p-value) across 100,000 random samplings is shown in FIG. 3. This figure shows average p-values for a sorted partitioning of N=50, k=from 2 to 48. Standard deviations of the average values are shown as error limits in dotted lines [labeled: log 10(p-value)+/−SD]. The binomial coefficient (N-chose-k) is displayed as solid line [labeled: −log 10(NchooseK)], and the dashed line is the mean p-value [labeled: mean log 10(p-value)]. All these are all plotted on a $\log_{10}$ scale. FIG. 4 shows $\log_{10}$ of the average p-values for a sorted partitioning of data sets having different numbers of values (N). In this figure, the average p-values for all possible sorted partitions (with a minimum partition size of 2) are shown for every third N value from N=2 to N=47.

These averaged curves can be well-represented by hyperbolic curves with appropriately fitted parameters or derived by analysis of the p-value function and the appropriate distribution. Alternatively, they can either be approximated using model averaging sets of random numbers. By these methods, the correction terms can be stored for retrieval as needed, calculated on the fly with an appropriate set of random data, or calculated using the appropriately fitted family curves, i.e. one curve for all k corresponding for each value of N.

To demonstrate the effectiveness of this method, we applied it to array 2-color (ratiometric) CGH measurements of copy number variation (CNV) of DNA extracted from healthy individuals. (see, Perry, J. Hiintart "The fine-scale and complex architecture of human copy-number variation", Am J Hum Genet. 2008 March; 82(3):685-95. Epub 2008 Jan. 24). The experimental data represents the log-ratios of measurements of CGH probe hybridization of genomic DNA from unknown samples relative to a reference sample. The unknown samples in this case represent the genomic DNA of 30 individuals selected from 3 populations and one of unknown origin. The corresponding hybridization signals of both the unknown samples and reference sample are quantified and $\log_2$ ratio values are reported for each probe for each sequence. In most cases, variations are detected for multiple consecutive probes in more than one individual, and as such we average the values across common sets of probes for each of the samples. These are shown for several different individuals in FIGS. 5a to 5d, each of which show the identification of three distinct modes (or clusters) according to one embodiment of the present invention. As noted in the each figure, the Modality Method is: mean(log(p-value))+std(log (p-value), where "std" is standard deviation. The mean(Log 2(ratio)) values for probes to the indicated genomic regions (noted at the bottom of the figure) are shown in the top panel of each figure (with the standard error of the mean (SEM) indicated by the error bars). The calculated Modality Score plot is shown in the bottom panel of each figure.

Figure 5A:
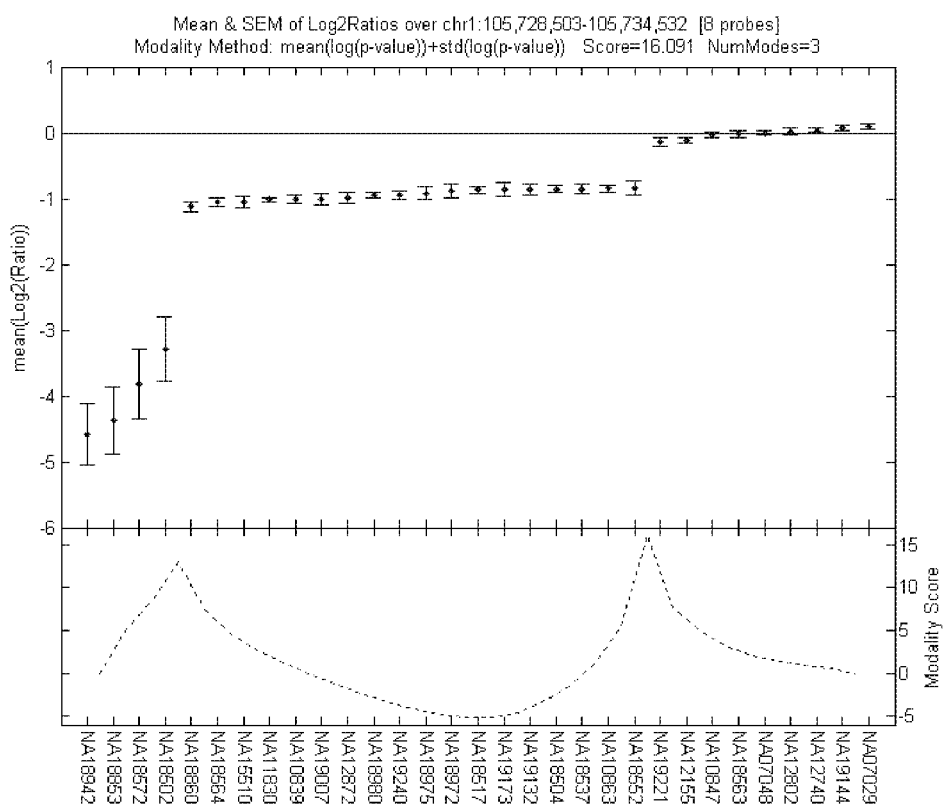
FIGS. 5a, 5b, 5c and 5d each show the identification of three distinct modes (or clusters) according to one embodiment of the present invention. As noted in the each figure, the Modality Method is: mean(log(p-value))+std(log(p-value), where "std" is standard deviation. The mean(Log 2(ratio)) values for probes to the indicated genomic regions (noted at the bottom of the figure) are shown in the top panel of each figure (with the standard error of the mean (SEM) indicated by the error bars). The calculated Modality Score plot is shown in the bottom panel of each figure.
Figure 5B:
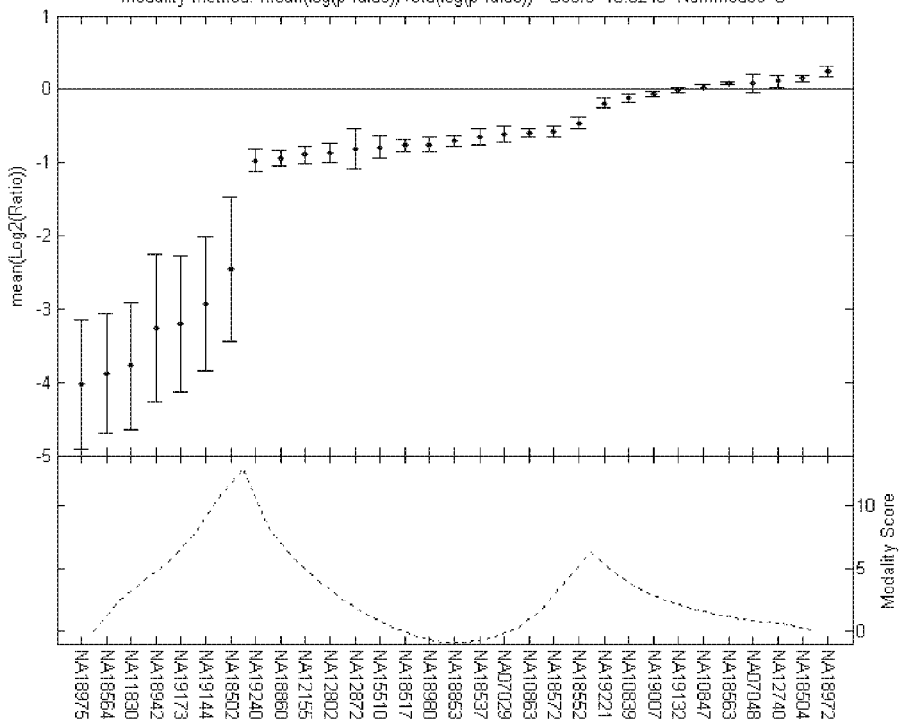
Figure 5C:
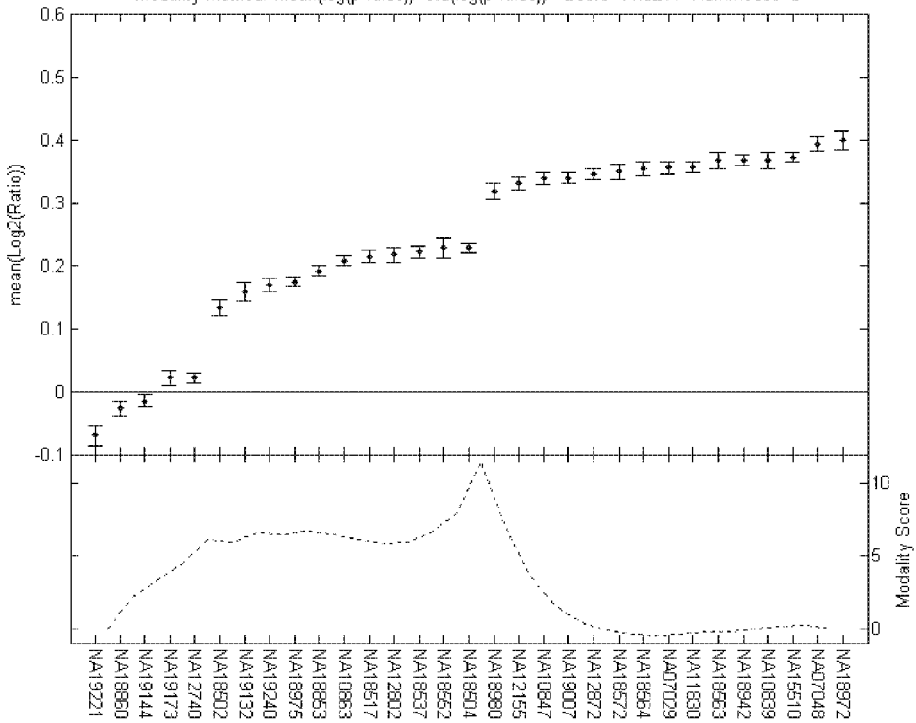
Figure 5D:
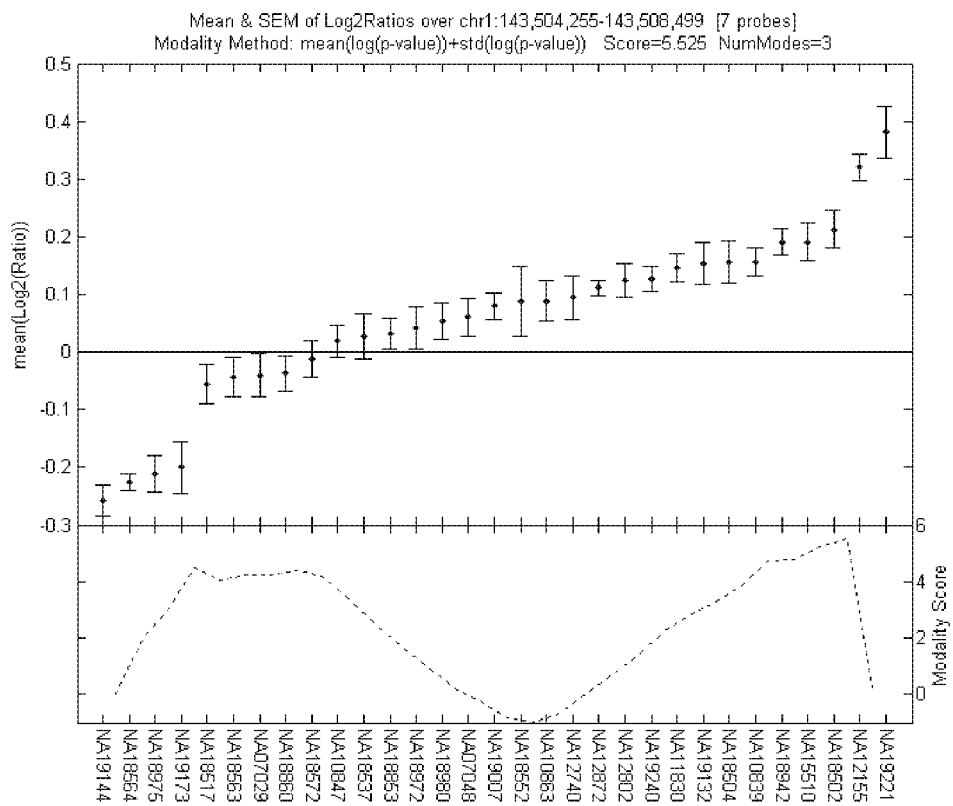

In FIG. 5a, 3 copy number states are identified suing the Modality Method, these states being clearly discernable by eye. FIGS. 5b, 5c and 5d show other exemplary partitioning of copy number sates, where in some cases the actual copy number states are more ambiguous. For example, the Modality Score of FIG. 5b provides an indication of a possible second breakpoint (between NA18552 and NA19221) that is not immediately discernable by eye.

Figure 6:
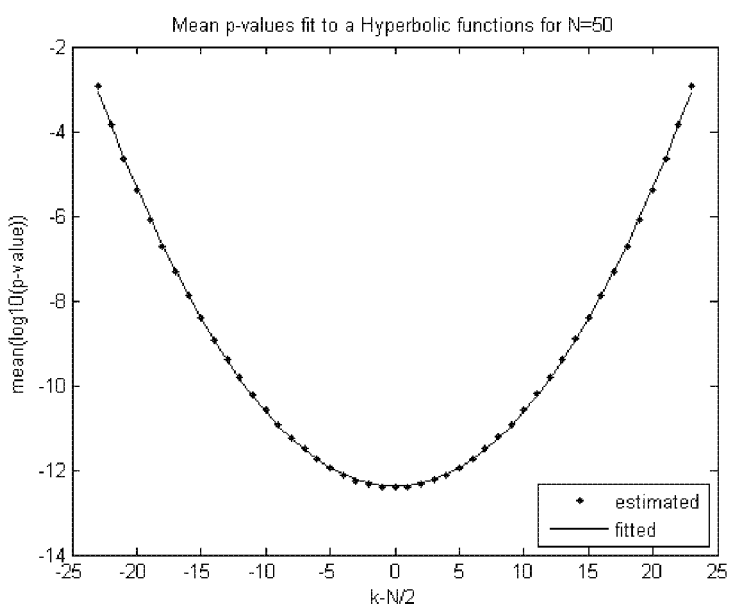
FIG. 6 is provided to demonstrate that the functional form of the mean p-values fit to a hyperbolic curve. The mean p-values are shown (diamonds) along with the $\log_{10} (B(N,k))$ estimate (solid line), where the parameters of the hyperbolic curve were manually-adjusted, indicating a non-linear optimization of parameters could accomplish an even better fit to the data.

For a known distribution, these correction factors can be estimated by either random number generation techniques, or by permutation of experimental data. In either case, such modeling processes can be too time consuming to be done on the fly during data analysis. In these cases, a more practical approach is to fit the modeled data to functional curves, such as polynomials, hyperbolic functions, cubic-splines, etc. One example of such a fit is shown in FIG. 6. In this case a hyperbolic curve (solid line) is shown to well represent the shape of the mean(p-value) data points (diamonds) determined by random number generation of Gaussian noise.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of clustering a data set from a biological assay, said method comprising:
    a) obtaining a data set from a biological assay, wherein said data set comprises N measured values;
    b) sorting said data set from low (sample 1) to high (sample N) based on said measured values;
    c) selecting a set of cut-off points, wherein each of said cut-off points (k) is selected from sample 2 to sample N−2 of said data set;
    d) determining, using a computer, the best cut-off point from said set of cut-off points, comprising;
        i) for each cut-off point k, bisecting said data set into a first subset comprising samples 1 to k and a second subset comprising samples (k+1) to N; calculating the p-value of the measured values in said first and second subsets using a 2-tailed t-test; and calculating a modality score based on said p-value; and
        ii) determining the best cut-off point based on said modality score;
    e) clustering said samples into a first and second group at said best cut-off point if said modality score exceeds a threshold value; and
    f) providing the result of said clustering step (e) to a user in a user-readable format.

2. The method of claim 1, wherein said two-tailed t-test is a Student's two-tailed t-test.

3. The method of claim 1, wherein said modality score employs a correction coefficient.

4. The method of claim 3, wherein said correction coefficient is a binomial correction coefficient B(N, k).

5. The method of claim 4, wherein said binomial correction coefficient B(N, k) is:

$N!/[k!(N-k)!]$.

6. The method of claim 4, wherein said binomial correction coefficient B(N, k) is:

$N!^{0.5}/[k!(N-k)!]^{0.5}$.

7. The method of claim 3, wherein said correction coefficient is based on an average p-value calculated using multiple random data sets, wherein each of said multiple random data sets has N values and wherein p-values for each of said multiple random data sets are calculated using said selected cut-off points for said data set.

8. The method of claim 7, wherein said multiple random data sets are generated using one or more of: a random number generator and a random permutation of measured data.

9. The method of claim 7, wherein said correction coefficient is based on a combination of said average p-value and an additional statistic.

10. The method of claim 9, wherein said additional statistic is selected from: standard deviation of said average p-value and the intra-quartile range (IQR) of said average p-value.

11. The method of claim 1, wherein said method further comprises repeating said method iteratively or recursively on one or both of said first and second groups.

12. The method of claim 1, wherein said biological assay is selected from the group consisting of: an array-based assay, an ELISA assay, a PCR assay, a RT-PCR assay, a quantitative RT-PCR assay, a flow cytometric assay, a reporter gene assay, and a high throughput screening assay.

13. A system for clustering a data set from a biological assay, said system comprising:
    a computer comprising:
    (a) a communication module comprising an input manager for receiving input from a user and an output manager for communicating output to a user;
    (b) a processing module comprising a biological assay data clustering manager configured to:
        (i) receive a biological assay data set comprising N measured values from a user;
        (ii) sort said data set from low (sample 1) to high (sample N) based on said measured values;
        (iii) select a set of cut-off points, wherein each of said cut-off points (k) is selected from sample 2 to sample N−2 of said sorted data set;
        (iv) determine the best cut-off point from said set of cut-off points, comprising;
            1) for each cut-off point k, bisecting said data set into a first subset comprising samples 1 to k and a second subset comprising samples (k+1) to N; calculating the p-value of the measured values in said first and second subsets using a 2-tailed t-test; and calculating a modality score based on said p-value; and
            2) determining the best cut-off point based on said modality score;

v) cluster said samples into a first and second group at said best cut-off point if said modality score exceeds a threshold value; and vi) provide the result of said clustering step (v) to said user in a user-readable format.

14. The system of claim 13, wherein said two-tailed t-test is a Student's two-tailed t-test.

15. The system of claim 13, wherein said modality score employs a binomial correction coefficient B(N, k).

16. The system of claim 15, wherein said binomial correction coefficient B(N, k) is selected from: $N!/[k!(N-k)!]$ and $N!^{0.5}/[k!(N-k)!]^{0.5}$.

17. The system of claim 13, wherein said modality score employs a correction coefficient based on an average p-value calculated using multiple random data sets, wherein each of said multiple random data sets has N values and wherein p-values for each of said multiple random data sets are calculated using said selected cut-off points for said data set.

18. The system of claim 17, wherein said correction coefficient is based on a combination of said average p-value and an additional statistic selected from: standard deviation of said average p-value and the intra-quartile range (IQR) of said average p-value.

19. The system of claim 13, wherein said biological assay data clustering manager is further configured to repeat steps (ii) to (v) iteratively or recursively on one or both of said first and second groups.

20. A physical computer program product comprising a computer readable medium carrying one or more sequences of instructions for clustering a data set from a biological assay, wherein execution of one or more sequences of instructions by one or more processors causes the one or more processors to perform the steps of:

a) receiving a data set from a biological assay from a user, wherein said data set comprises N measured values;

b) sorting said data set from low (sample 1) to high (sample N) based on said measured values;

c) selecting a set of cut-off points, wherein each of said cut-off points (k) is selected from sample 2 to sample N−2 of said data set;

d) determining the best cut-off point from said set of cut-off points, comprising;
  i) for each cut-off point k, bisecting said data set into a first subset comprising samples 1 to k and a second subset comprising samples (k+1) to N; calculating the p-value of the measured values in said first and second subsets using a 2-tailed t-test; and calculating a modality score based on said p-value; and
  ii) determining the best cut-off point based on said modality score;

e) clustering said samples into a first and second group at said best cut-off point if said modality score exceeds a threshold value; and f) providing the result of said clustering step (e) to said user in a user-readable format.

\* \* \* \* \*